United States Patent [19]

Bezoari

[11] Patent Number: 4,727,176

[45] Date of Patent: Feb. 23, 1988

[54] HYDROXYMETHYLPHENOXYPHOSPHA-ZENES AND A PROCESS FOR PRODUCING SAME

[75] Inventor: Massimo D. Bezoari, Baton Rouge, La.

[73] Assignee: The Dow Chemical Company, Midland, Mich.

[21] Appl. No.: 912,892

[22] Filed: Sep. 29, 1986

[51] Int. Cl.$^4$ .............................. C07F 9/24
[52] U.S. Cl. ...................................... 558/080
[58] Field of Search ........................................ 558/80

[56] References Cited

U.S. PATENT DOCUMENTS

| | | | |
|---|---|---|---|
| 3,206,494 | 9/1965 | Lund et al. | 260/461 |
| 3,240,728 | 3/1966 | Lund | 260/2.5 |
| 3,446,876 | 5/1969 | Breslow | 260/927 |
| 3,462,518 | 8/1969 | Kober et al. | 260/927 |
| 4,029,634 | 6/1977 | Meredith | 260/45.9 NP |
| 4,107,108 | 8/1978 | Dieck et al. | 521/85 |
| 4,117,041 | 9/1978 | Guechl | 260/927 N |
| 4,124,557 | 11/1978 | Dieck et al. | 260/30.6 R |
| 4,179,555 | 12/1979 | Cheng et al. | 528/168 |
| 4,601,843 | 7/1986 | Carr et al. | 558/80 |

OTHER PUBLICATIONS

Kajiwara et al, "Phosphonitrilic Chloride: 23. Substitution Reaction of Phosphonitrilic Chloride Trimer with Sodium Hydroxymethylphenolate and Polymerization of Substitution Products", Polymer, 1975, vol. 16, Jan., 21–24.

Primary Examiner—Anton H. Sutto
Attorney, Agent, or Firm—E. E. Spielman; D. R. Howard

[57] ABSTRACT

This invention relates to $R_1$, i.e., phenoxy-, halophenoxy- and isopropoxy- hydroxymethylphenoxycyclotriphosphazenes and to a process for their preparation. The process comprises reacting $R_1$-chlorocyclotriphosphazene with a salt of hydroxymethylphenoxide. The reaction takes place in the presence of an inert organic solvent and at a temperature within the range of from about 20° C. to about 150° C. The invention also relates to $R_1$-hydroxymethylphenoxycyclotetraphosphazenes. Also disclosed is a process for preparing a mixture of $R_1$-hydroxymethylcyclotriphosphazene and $R_1$-hydroxymethylcyclotetraphosphazene by reacting a mixture of $R_1$-chlorocyclotriphosphazene and $R_1$-chlorocyclotetraphosphazene with a hydroxymethylphenoxide salt.

35 Claims, No Drawings

HYDROXYMETHYLPHENOXYPHOSPHAZENES AND A PROCESS FOR PRODUCING SAME

BACKGROUND OF THE INVENTION

This invention relates to isopropoxy-, phenoxy- and halophenoxy- hydroxymethylphenoxycyclotriphosphazenes and to a process for producing same.

It is well known that the presence of phosphorus in polymeric materials imparts flame retardant properties to these materials. Flame retardancy is further enhanced by the synergistic effect of the combined presence of nitrogen and phosphorus, as provided by phosphazenes, for example. It is well recognized by those skilled in this art and should be clearly understood by others, however, that all known organic polymers will burn when subjected to a sufficiently intense heat source, whether or not they contain a fire retardant additive.

One disadvantage of using common flame retardants is that they contain significant amounts of chlorine and/or bromine which are evolved as gaseous hydrogen chloride and hydrogen bromide under fire conditions. Such evolution is undesirable in case of fires in closed areas in which people are present. Another drawback to these and other flame retardants is that they are generally present in the formulated polymeric material as an additive. Since they are not bonded to the polymer, they have a tendency, over a period of time, to leach out of the material, thus decreasing their effectiveness and causing possible toxicity hazards.

The use of hydroxymethylphenoxycyclotriphosphazenes as flame retardants in a polymeric formulation avoids both the problem of hydrogen chloride and hydrogen bromide generation and the problem of flame retardant leaching. The former problem is diminished as the hydroxymethylphenoxycyclotriphosphazene can be selected to contain little or no chlorine or bromine while the latter problem is greatly reduced as the hydroxymethylphenoxycyclotriphosphazene copolymerizes, via its hydroxymethylphenoxy functional groups, with the polymeric material.

Due to the value of such hydroxymethylphenoxycyclotriphosphazenes, it is desirable that an efficient, simple process be made available for their manufacture.

It is therefore an object of this invention to provide isopropoxy- and phenoxy- hydroxymethylphenoxycyclotriphosphazenes and a process for producing same.

THE INVENTION

In one embodiment, this invention relates to a process for the production of hydroxymethylphenoxycyclotriphosphazenes of the formula:

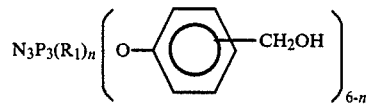

(A)

wherein $R_1$ is an isopropoxy radical of the formula

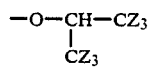

or an aryloxy radical of the formula,

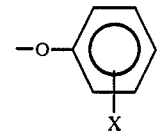

wherein each Z substituent is independently selected for each isopropoxy radical from F and H, wherein each X substituent is independently selected for each aryloxy radical from Cl, Br, F and H, and wherein n is a whole integer which is $\geq 1$ and $\leq 5$, when said hydroxymethylphenoxycyclotriphosphazene has an m- or p- hydroxymethylphenoxy substituent, and which is $\geq 3$ and $\leq 5$, when said hydroxymethylphenoxycyclotriphosphazene has an o-hydroxymethylphenoxy substituent. Since Z and X are each independently selected for, respectively, each isopropoxy and aryloxy radical substituent, $R_1$ can represent different radicals in combination. For example, when $R_1$ is an aryloxy, $R_1$ can represent the combination of diphenoxy-(4-bromophenoxy)-(3-chlorophenoxy). See Example 2. Similarly, if $R_1$ is an isopropoxy radical, $R_1$ can represent the combination diisopropoxy-(1,3-difluoroisopropoxy).

The process comprises reacting an $R_1$-chlorocyclotriphosphazene having n $R_1$ substituents and (6-n) chloride constituents with a salt of hydroxymethylphenoxide for a time period sufficient to yield the desired hydroxymethylphenoxycyclotriphosphazene. The reaction occurs in the presence of an inert, organic solvent medium and at a temperature within the range of from about 20° C. to about 150° C. The molar ratio of the $R_1$-chlorocyclotriphosphazene reactant to the hydroxymethylphenoxide anion constituent of the salt is 1:b in which b>5-n. Improved yields—indeed, yields up to 100%—can be achieved if $B \geq 6-n$.

The subject process may be represented by:

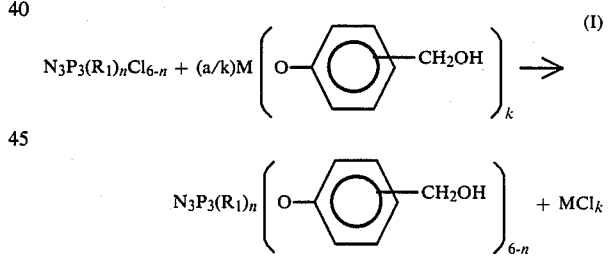

(I)

wherein: $R_1$ and n are as previously defined; M is an inorganic cation, preferably a metal such as Na, K, Li, Ca, Mg, and the like; k is the oxidation state of M and is 1 or 2; and a is greater than 5-n. It is to be understood that the formula

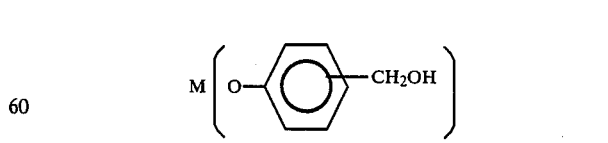

can represent a single salt, i.e., an p-hydroxymethylphenoxide, an m-hydroxymethylphenoxide, or an o-hydroxymethylphenoxide, or can represent a mixture of such salts. As can be seen, the identity of the particular $R_1$-hydroxymethylphenoxycyclotriphosphazene is dependent upon the identity of $R_1$, the hydroxymethyl ring location and the value of n found in the two reactants. For example, if triphenoxy-tris(p-hydroxymethylphenoxy)cyclotriphosphazene is the desired product, then the reactants, triphenoxy-trichlorocyclophosphazene and a salt of p-hydroxymethylphenoxide are used. Further, if the desired product is mono(1,1,1,3,3,3-hexafluoroisopropoxy)-penta(p-hydroxymethylphenoxy)cyclotriphosphazene, then the reactants are mono(1,1,1,3,3,3-hexafluoroisopropoxy)-pentachlorocyclotriphosphazene and a salt of p-hydroxymethylphenoxide.

This invention also relates to the compound:

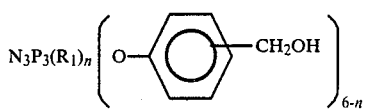
(B)

wherein $R_1$ and n are as previously defined.

This invention further relates to the following compound and to a process for its production. The compound is in accordance with the formula:

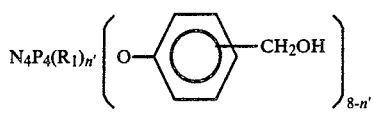
(C)

wherein $R_1$ is as previously defined and n' is a whole integer which is $\geq 1$ and $\leq 7$ when said hydroxymethylphenoxycyclotriphosphazene has an m- or p- hydroxymethylphenoxy substituent and which is $\geq 4$ and $\leq 7$ when said hydroxymethylphenoxycyclotriphosphazene has an o-hydroxymethylphenoxy substituent.

The hydroxymethylphenoxy substituents are the basic functional groups of the compounds (A), (B) and (C) while the $R_1$ substituents are either inert or functional groups. For example, the $R_1$ substituents are basically inert if they are isopropoxy or phenoxy. Functional $R_1$ groups, such as those contributing to flame retardancy, are exemplified by halophenoxide. Fluoro groups are known to impart other properties such as thermal stability and adhesive resistance.

In process (I), the particular inert solvent used is not critical. The solvent need only be inert in the reaction system and be capable of solubilizing the reactants under reaction conditions For example, solvents such as octane, heptane, hexane, cyclohexane, benzene, toluene, xylene, diglyme, triglyme, tetraglyme, tetrahydrofuran and dioxane are all suitable. To achieve convenient temperature control, the process of this invention is preferably run at reflux conditions and, thus, in these preferred cases, the solvent used is one which will provide reflux at the chosen process temperature. A preferred solvent is tetrahydrofuran as it provides good solubility and reflux at a temperature of from about 60° C. to about 70° C.

The process is generally run within the temperature range of from about 50° C. to about 140° C. High yields are obtained when the process temperature is within the range of from about 60° C. to about 70° C. Temperatures substantially lower than 50° C., e.g., 0° C., may very well produce the $R_1$-hydroxymethylphenoxycyclotriphosphazene product sought; however, the yield is predicted to be low and reaction times long. Temperatures much in excess of 140° C. are not desirable as it is expected that some inter- and intramolecular cross-linking will occur. Such cross-linking lowers the yield of the product. When temperatures above 70° C. are used, it is preferred that the process be initiated at a lower temperature, say about 20° C. to about 50° C., followed by the raising of the temperature up to the selected level. By providing such a temperature profile over process time, the formation, during the initial phase of the process, of undesirable cross-linked products is avoided.

The reaction time for the process of this invention should be sufficiently long to achieve the desired hydroxymethylphenoxy substitution of the chloride constituents initially present in the $R_1$-chlorocyclotriphosphazene reactant. The rate of substitution is interrelated with process temperature. After process initiation, the higher the temperature used, the shorter the reaction period will be. Generally speaking, for the temperature range of 50° C. to 140° C., the reaction period will be about 200 hours for the lower end of the range to about 50 hours for the upper end of the range. For the temperature range of 60° C. to 70° C., the reaction period will be within the range of from about 170 hours to about 70 hours.

While the subject process is preferably run under reflux conditions, it is to be understood, that reflux conditions need not be used, but instead, can be replaced by other temperature control techniques, such as by reactor immersion in a controlled temperature bath.

The order of addition of the $R_1$-chlorocyclotriphosphazene and the hydroxymethylphenoxide salt reactants is not critical. However, agitation, e.g., stirring, is useful in ensuring uniformity of reactant concentrations in the reaction mix.

The determination of a minimum molar ratio of the $R_1$-chlorocyclotriphosphazene to the hydroxymethylphenoxide anion component of the salt reactant is dependent upon the chloride content of the former. As there are 6-n chlorides in each molecule of the phosphazene reactant, the minimum molar ratio of phosphazene reactant to hydroxymethylphenoxide anion which is needed to give some yield of the $R_1$-hydroxymethylphenoxycyclotriphosphazene product is 1:b wherein b > 5-n. Since reaction yield is determinative of process efficiency, a molar ratio when b = 6-n is preferred as such ratio provides the minimum amount of hydroxymethylphenoxy anions needed to replace all of the chlorides in the phosphazene reactant. Generally, a slight molar excess, say, 1 mole percent to about 10 mole percent, of hydroxymethylphenoxide anion will be used to ensure complete chloride substitution. Molar ratios in which 6-n > b > 5-n can be used to produce mixes of partially chloride substituted and completely chloride substituted $R_1$-hydroxymethylphenoxycyclotriphosphazene product. Such mixes may provide the property sought and thus, in these cases, further chloride substitution may not represent a correct economical choice.

As before noted, the $R_1$-chlorocyclotriphosphazene reactant has the formula:

wherein $R_1$ and n are defined as above. Exemplary of such reactants are: isopropoxy-pentachlorocyclotriphosphazene; tri(1,1,3,3-tetrafluoroisopropoxy)trichlorocyclotriphosphazene; tri(1,1,1,3,3,3-hexafluoroisopropoxy)-trichlorotriphosphazene; triisopropoxy-trichloro-cyclotriphosphazene; tetraisopropoxy-dichlorocyclotriphosphazene; diphenoxytetrachlorocyclo-triphosphazene; triphenoxy-trichlorocyclotriphosphazene; tetraphenoxy-dichlorocyclotriphosphazene; pentaphenoxy-monochlorocyclotriphosphazene; tri(o-chlorophenoxy)-trichlorocyclotriphosphazene; tetra(p-chlorophenoxy)-dichlorocyclotriphosphazene; penta(m-bromophenoxy)-monochlorocyclotriphosphazene; di(p-fluorophenoxy)-tetrachlorocyclotriphosphazene; and the like.

The $R_1$-chlorocyclotriphosphazene can be conveniently prepared in accordance with the following reaction:

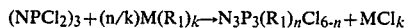

$$(NPCl_2)_3 + (n/k)M(R_1)_k \rightarrow N_3P_3(R_1)_nCl_{6-n} + MCl_k$$

wherein n, k, M and $R_1$ are as defined previously. The reaction occurs at a temperature within the range of from about 0° C. to about 150° C. and in the presence of an inert organic solvent. The $MCl_k$ salt will form a precipitate and can be filtered from the reaction mix. To ensure that the hexachlorocyclotriphosphazene is not subjected to a molar ratio of hexachlorocyclotriphosphazene to the $R_1$ anion component of the $M(R_1)_k$ salt greater than 1:n/k, the $M(R_1)_k$ salt is added slowly to the reaction mix with the reaction mix being continuously agitated, such as by stirring. The reaction is preferably run at reflux conditions so as to conveniently control the reaction temperature. With a reaction temperature above 60° C., the reaction time is about 0.5 hours to about 36 hours.

The $M(R_1)_k$ salt is conveniently prepared by the reaction of $R_1H$ with a base, such as NaH, to yield the $M(R_1)_k$ salt. The salt can also be purchased commercially. For example, the isopropoxide salt can be purchased from Morton Thiokol (Alfa), Inc.

The hydroxymethylphenoxide salt reactant has the formula:

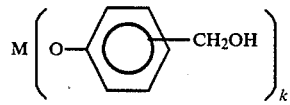

wherein M and k are as previously defined. Exemplary of suitable salts are: Sodium p-hydroxymethylphenoxide; potassium m-hydroxymethylphenoxide; calcium o-hydroxymethylphenoxide; and the like. Preferred salts are sodium o-, m- and p- hydroxymethylphenoxide.

The hydroxymethylphenoxide salt reactant can be prepared in accordance with the reaction:

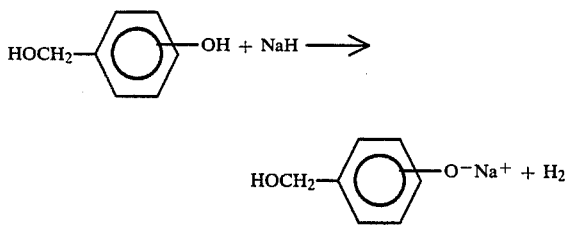

This reaction occurs in an inert organic solvent, which solvent is preferably the same solvent which is used in the $R_1$-chlorocyclotriphosphazene hydroxymethylphenoxide salt reaction. The reaction mix should be agitated, e.g., stirred, and is preferably run under reflux conditions. The order of addition of the reactants is not critical. The reaction temperature is within the rang of from about 0° C. to about 150° C. and the reaction runs for that period of time necessary to ensure complete reaction of the hydroxymethylphenol reactant. Such reaction time is preferably from about 0.5 hours to about 48 hours.

In another embodiment of this invention, a mixture of $R_1$-hydroxymethylphenoxycyclotriphosphazenes and $R_1$-hydroxymethylphenoxycyclotetraphosphazenes is produced. The process comprises the following reaction:

$$N_4P_4(R_1)_{n'}Cl_{8-n'} + N_3P_3(R_1)_nCl_{6-n} + \quad\quad (II)$$

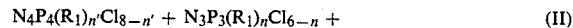

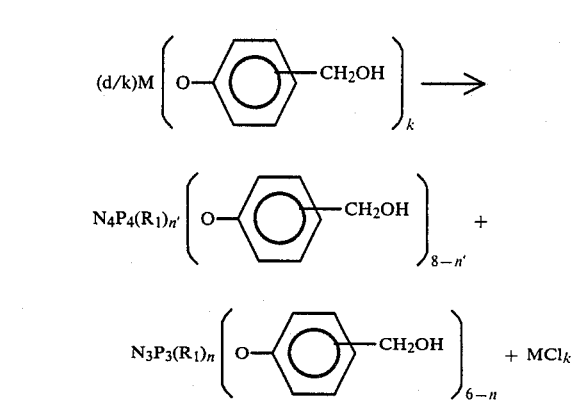

wherein: $R_1$, M, n, n', and k are as previously defined; and d is greater than 13-n'-n. The molar ratio of the trimer and tetramer to the hydroxymethylphenoxy anion component of the salt is 1:b, wheren $b \geq 13-n-n$. Generally, in the above reaction, the $R_1$-chlorocyclotetraphosphazene reactant can be seen to have a higher reactivity than the $R_1$-chlorocyclotriphosphazene reactant and thus, it is expected that complete chloride substitution of the former will occur first. Therefore, if full chloride substitution of the trimer is required, then the moles of hydroxymethylphenoxy anion needed per mole of phosphazene tetramer and trimer will be at least equal to a b value of 14-n'-n. If partial chloride substitution is acceptable for the final product mix, then a value for b between 13-n'-n and 14-n'-n is used. In this latter case, it is expected that the phosphazene trimer will be the product which will be partially chloride substituted due to the higher reactivity of the phosphazene tetramer.

The reaction occurs in an inert solvent and under the conditions similarly used in the process of this invention described previously for producing isopropoxy- and phenoxyhydroxymethylphenoxycyclotriphosphazenes, i.e., process (I).

The mixture of the phosphazene trimer and tetramer preferably has a molar ratio of the trimer to the tetramer of about 4:1 as such a mix is readily available from commercial phosphazene processes.

The hydroxymethylphenoxy salt reactant used above can be prepared in the same manner hereinbefore described.

The $R_1$-chlorocyclotriphosphazene and $R_1$-chlorocyclotetraphosphazene reactants used above are produced in accordance with:

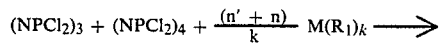

$$(NPCl_2)_3 + (NPCl_2)_4 + \frac{(n' + n)}{k} M(R_1)_k \longrightarrow$$

-continued

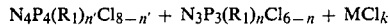

$$N_4P_4(R_1)_{n'}Cl_{8-n'} + N_3P_3(R_1)_nCl_{6-n} + MCl_k$$

wherein $R_1$, n, n', k and M are as previously defined. The same reaction conditions used in the before described process for producing $R_1$-chlorocyclotriphosphazene may be used in the instant reaction. The $M(R_1)_k$ salt is prepared as before noted.

The following examples are submitted for the purpose of further illustrating the nature of the present invention and are not to be construed as a limitation on the scope thereof.

The NMR spectroscopy used in analyzing the reaction products in various of the following Examples was 31P NMR spectroscopy. In general, the instrument, a JEOL 90X FT NMR, was locked onto acetone-d6, and the shift of 85% $H_3PO_4$ set to zero. Samples were analyzed in THF solution with a coaxial tube containing acetone-d6.

All spectra exhibited AB2 systems, the appearance of which varies, depending on the ratio of coupling constant, J, to chemical shift difference, v, as described in "Applications of Nuclear Magnetic Resonance Spectroscopy in Organic Chemistry," L. J. Jackman, S. Sternhell, Pergamon Press, London, 1969, pp. 130-132; "Organic Spectroscopy—An Introduction," S. F. Dyke, A. J. Floyd, M. Sainsbury, R. S. Theobald, Penguin, England, 1971, pp. 120-122; and "Nuclear Magnetic Resonance," W. W. Paudler, Allyn and Bacon, Boston, 1971, pp. 115-120. The chemical shifts gave good correlation with shifts reported for similar hydroxymethylphosphazenes in "Phosphorus-Nitrogen Compounds," H. R. Allcock; Acad Press, New York, 1972; and "The Chemistry of Phosphorus," J. Emsley, D. Hall, Harper and Row, London, 1976, p. 82. All of the just described references are incorporated herein as if fully set forth.

EXAMPLE 1

Preparation of Tetraphenoxy-bis(2-hydroxymethylphenoxy)cyclotriphosphazene

100% NaH (2.4 g, 0.1 mole) was slowly added to a solution of 2-hydroxybenzylalcohol (12.4 g, 0.1 mole) in tetrahydrofuran (THF), (150 mL), and the reaction stirred under nitrogen for 48 hours to yield a yellow slurry.

In a separate flask, 100% NaH (4.8 g, 0.2 mole) was added slowly to a solution of phenol (18.8 g, 0.2 mole) in 175 mL THF, with stirring under nitrogen. The reaction was left overnight. After heating to reflux, the hot solution was added dropwise to a refluxing solution of hexachlorocyclotriphosphazene (17.3 g, 0.05 mole) in THF (150 mL), giving an immediate white precipitate throughout the addition. Reflux was continued for 2-3 hours.

THF (200 mL) was added to the yellow slurry of sodium hydroxymethylphenolate, and the mixture heated to reflux until the precipitate dissolved. The hot solution was poured into the refluxing solution of dichloro-tetraphenoxyphosphazene and refluxing continued for 4 hours, during which the yellow color disappeared, leaving an NaCl precipitate. The reaction mix was allowed to cool, filtered, and the filtrate evaporated at reduced pressure to give a viscous amber oil.

The weight of the dried NaCl precipitate was 15.5 g (0.27 mole), indicating a yield of 90%.

Analysis of the viscous amber oil by 31P NMR spectroscopy showed a major absorption peak at $-8.3$ ppm, corresponding to the desired product. Other small peaks were observed in the regions $-4 \rightarrow -10$ ppm, which is the region for diaryloxy-substituted P nuclei in phosphazene cyclic trimers, $-11 \rightarrow -17$ ppm, ascribed to P nuclei with one chloride and one aryloxy substituent, and $-18 \rightarrow -23$ ppm for dichloro-substituted (unreacted) P nuclei. The relative ratio of diaryloxy- : monoaryloxy-monochloro- : dichloro-substituted phosphorus was 16: 4: 1. Thus, one phosphorus dichloride unit remained unsubstituted per seven phosphazene trimer rings, under these reaction conditions.

The infrared spectrum of the product showed absorptions centered at (wavenumbers): 3400 (O-H); 3080 (Ph-H); 1600, 1490 (Ar); 1270, 1180 (P=N and Ar-O).

EXAMPLE 2

Preparation of (2-Hydroxymethylphenoxy)-diphenoxy-(4-bromophenoxy)-(3-chlorophenoxy)-(3-hydroxymethylphenoxy) Cyclotriphosphazene Sodium hydride (5.0 g, 0.21 mole) was slowly added to a solution of phenol (9.4 g, 0.1 mole), p-bromophenol (8.6 g, 0.05 mole), and m-chlorophenol (6.4 g, 0.05 mole) in THF (300 mL), and the slurry heated at 60° C. for about 3 hours. The resulting solution was then added dropwise to solution of hexachlorocyclotriphosphazene (17.3 g, 0.05 mole) in THF (150 mL) at 60° C., with stirring (all reactions under nitrogen), and the resulting mixture heated at 60°-67° C. for 4 hours.

A sample of the reaction mixture was analyzed by 31P NMR spectroscopy. The spectrum indicated superimposed patterns due to an A3 system (singlet at $-19$ ppm ascribed to tri(aryloxy)-trichloro-cyclotriphosphazene, an AB2 system (2nd order spectrum) ascribed to tetra(aryloxy)-dichlorocyclotriphosphazene, and a second AB2 system which was assigned to a small amount of penta(aryloxy)-monochlorocyclotriphosphazene, relative ratio about 1:7:2.

In a separate flask, sodium hydride (2.6 g, 0.11 mole) was slowly added to a solution of o-hydroxymethylphenol (6.7 g, 0.05 mole) and m-hydroxymethylphenol (6.7 g, 0.05 mole) in THF (250 mL), and the reaction heated at 60° C. for 18 hours. The product was added all at once to the reaction mixture above, and the mix was heated at 60°-67° C. for about 1 week. The slurry was allowed to cool, and about 300 mL water added. After mixing in a separatory funnel, the THF layer was separated, dried over $MgSO_4$, and the solvent evaporated yielding an amber oil. The aqueous layer was neutral to pH paper.

A sample of the amber oil obtained above was analyzed by 31P NMR spectroscopy. Three peaks were observed only in the region $-8 \rightarrow -11$, at $-8.2$, $-9.5$, and $-10.1$ ppm, indicating the all P nuclei were completely substituted by aryloxy groups. The relative ratio of these was 6:3:1, which gave good correspondence with the ratio for the intermediate mixture. The signals wer therefore ascribed to bis(hydroxymethylphenoxy)-tetra(aryloxy)cyclotriphosphazene, tris(hydroxymethylphenoxy)-tris(aryloxy)cyclotriphosphazene, hydroxymethylphenoxy-penta(aryloxy)cyclotriphosphazene, respectively.

EXAMPLE 3

Reaction of a Hexachlorocyclotriphosphazene and Octachlorocyclotetraphosphazene Mixture Phenol (10.34 g, 0.11 mole), m-chlorophenol (6.08 g, 0.048 mole), and p-bromophenol (8.17 g, 0.048 mole) were dissolved in about 300 mL THF, and sodium hydride (4.92 g, 0.21 mole) added slowly, with stirring, under nitrogen. The slurry was heated at 60° C. for about 18 hours to yield a suspension. The suspension was then added dropwise to a refluxing solution of hexachlorocyclotriphosphazene and octachlorocyclotetraphosphazene (4:1; 17.3 g, 0.15 mole of $NPCl_2$ units) in THF (about 150 mL). The reaction was heated at 60°–67° C. for 24 hours. A sample of the reaction solution was filtered and submitted for 31P NMR analysis.

The resulting spectrum showed resonance signals at $+7 \rightarrow +10$ ppm, and $+13 \rightarrow +18$ ppm due to monochloromonoaryloxy and diaryloxy phosphorus nuclei respectively, in the tetrameric ring. Thus, the characteristic A2B2 system indicated that the desired dichlorohexa(aryloxy)cyclotetraphosphazene was obtained. Resonance signals were also observed at $-2 \rightarrow -8$ ppm, and $-17 \rightarrow -22$ ppm. These were ascribed to a mixture of trichloro-tris(aryloxy)cyclotriphosphazene, and dichloro-tetra(aryloxy)cyclotriphosphazene (relative ratio about 1:1). A trace amount of monochloro-penta(aryloxy)cyclotriphosphazene was also present.

In a separate reaction (also under nitrogen), hydroxymethylphenol (a 1:1 mixture of o- and m- isomers, total weight 12.8 g, 0.095 mole) was dissolved in THF (150 mL). Sodium hydride (2.3 g, 0.096 mole) was added slowly, and the resulting suspension was heated at 60°–67° C. for 24 hours, then added all at once to the chloroaryloxycyclotetra and tri- phosphazene product prepared as above. The reaction was heated at 60°–67° C. for about 4 days. The resultant reaction product was filtered, and the filtrate concentrated by evaporation at reduced pressure. A sample was analyzed by 31P NMR spectroscopy. The spectrum revealed that all the phosphorus nuclei in the tetramer rings were now aryloxy-substituted, showing that the desired bis(hydroxymethylphenoxy)-hexa(aryloxy)cyclotetraphosphazene was obtained. Resonance signals due to the cyclic trimers revealed that the major constituents of the mixture were bis(hydroxymethylphenoxy)-tetra(aryloxy)cyclotriphosphazene, tris(hydroxymethylphenoxy)-tris(aryloxy)cyclotriphosphazene, and chloride-containing intermediates. The relative amounts of these trimers were about 1:1:2.

EXAMPLE 4

Reaction of Hexachlorocyclotriphosphazene and Octohexachlorotetraphosphazene Mixture The same procedure in Example 3 was repeated, except that the final reaction was allowed to proceed for 7 days at 60°–67° C. The resulting mixture gave similar spectroscopic results, except that the relative ratio of bis(hydroxymethylphenoxy)-tetra(aryloxy)-cyclotriphosphazene to tris(hydroxymethylphenoxy)-tris(aryloxy)-cyclotriphosphazene to mono(hydroxymethylphenoxy)-penta(aryloxy)-cyclotriphosphazene to chloride-containing intermediates was about 4:1:4.

I claim:

1. A process for the production of a hydroxymethylphenoxycyclotriphosphazene of the formula,

wherein $R_1$ is an isopropoxy radical having the formula

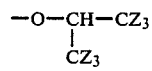

or an aryloxy radical having the formula

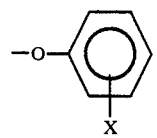

wherein each Z is independently selected for each isopropoxy radical from F and H, wherein each X is independently selected for each aryloxy radical from Cl, Br, F and H, and wherein n is a whole integer which is $\geq 1$ and $\leq 5$ when said compound has an m- or p- hydroxymethylphenoxy substituent and which is $\geq 3$ and $\leq 5$ when said compound has an o-hydroxymethylphenoxy substituent, said process comprising, reacting an $R_1$-chlorocyclotriphosphazene having n $R_1$ substituents and 6-n chloride constituents and a salt of hydroxymethylphenoxide for a time period sufficient to yield said hydroxymethylphenoxycyclotriphosphazene, said reaction occurring in an inert organic solvent medium, at a temperature within the range of from about 20° C. to about 150° C., and with a molar ratio of said $R_1$-chlorocyclotriphosphazene to said salt of the hydroxymethylphenoxide anion component of said salt of 1:b wherein b > 5-n.

2. The process of claim 1 wherein said salt is an alkali metal salt.

3. The process of claim 1 wherein said salt is a sodium hydroxymethylphenoxide salt.

4. The process of claim 1 wherein said temperature is within the range of from about 50° C. to about 140° C.

5. The process of claim 1 wherein n is 3 or 4.

6. The process of claim 1 wherein b is $\geq 6$-n.

7. The process of claim 1 wherein $R_1$ is said aryloxy radical.

8. The process of claim 1 wherein $R_1$ is said aryloxy radical and all X's are H.

9. The process of claim 8 wherein n is 3 or 4.

10. The process of claim 1 wherein $R_1$ is said isopropoxy radical.

11. The process of claim 1 wherein $R_1$ is said isopropoxy radical and all Z's are H.

12. The process of claim 11 wherein n is 3 or 4.

13. The process of claim 9 wherein said b $\geq 6$-n.

14. The process of claim 12 wherein said b $\geq 6$-n.

15. The process of claim 3 wherein n is 3 or 4, $R_1$ is said aryloxy radical and all X's are H and b $\geq 6$-n.

16. The process of claim 3 wherein n is 3 or 4, $R_1$ is said isopropoxy radical and all Z's are H and b $\geq 6$-n.

17. Compounds of the formula,

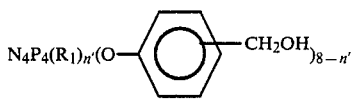

wherein $R_1$ is an isopropoxy radical having the formula

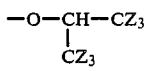

or an aryloxy radical having the formula

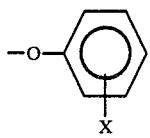

wherein each Z is independently selected for each isopropoxy radical from F and H, wherein each X is independently selected for each aryloxy radical from Cl, Br, F and H, and wherein n' is a whole integer which is $\geq 1$ and $\leq 7$ when said compound has an m- or p- hydroxymethylphenoxy substituent and which is $\geq 4$ and $\leq 7$ when said compound has an o-hydroxymethylphenoxy substituent.

18. A process for the production of a mixture of hydroxymethylphenoxycyclotriphosphazenes and hydroxymethylphenoxycyclotetraphosphazenes of the formulas, respectively,:

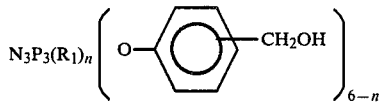

and

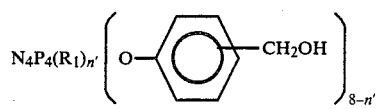

wherein $R_1$ is an isopropoxy radical having the formula

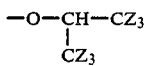

or an aryloxy radical having the formula

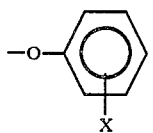

wherein each Z is independently selected for each isopropoxy radical from F and H, wherein each X is independently selected for each aryloxy radical from Cl, Br, F and H, and wherein n is a whole integer which is $\geq 1$ and $\leq 5$ when said hydroxymethylphenoxycyclotriphosphazene has an m- or p-hydroxymethylphenoxy substituent and which is $\geq 3$ and $\leq 5$ when said hydroxymethylphenoxycyclotriphosphazene has an o-hydroxymethylphenoxy substituent, and n' is a whole integer which is $\geq 1$ and $\leq 7$ when said hydroxymethylphenoxycyclotetraphosphazene has an m- or p- hydroxymethylphenoxy substituent and which is $\geq 4$ and $\leq 7$ when said hydroxymethylphenoxycyclotetraphosphazene has an o-hydroxymethylphenoxy substituent, said process comprising, reacting a mixture of $R_1$-chlorocyclotriphosphazene having n $R_1$ substituents and 6-n chloride constituents and $R_1$-chlorocyclotetraphosphazene having n' $R_1$ substituents and 8-n' chloride constituents, with a salt of hydroxymethylphenoxide for a time period sufficient to yield said hydroxymethylphenoxycyclotriphosphazene and said hydroxymethylphenoxycyclotetraphosphazene, said reaction occurring in an inert organic solvent medium, at a temperature within the range of from about 20° C. to about 150° C., and with a molar ratio of said $R_1$-chlorocyclotriphosphazene and said $R_1$-chlorocyclotetraphosphazene to the hydroxymethylphenoxide anion component of said salt of 1:b wherein b>13-n'-n.

19. The process of claim 18 wherein the molar ratio of said $R_1$-chlorocyclotriphosphazene to said $R_1$-chlorocyclotetraphosphazene is about 4:1.

20. The process of claim 18 wherein said salt is an alkali metal salt.

21. The process of claim 18 wherein said salt is a sodium hydroxymethylphenoxide salt.

22. The process of claim 18 wherein said temperature is within the range of from about 50° C. to about 140° C.

23. The process of claim 18 wherein n is 3, 4, or 5, and n' is 6.

24. The process of claim 18 wherein said $b \geq 14$-n-n'.

25. The process of claim 18 wherein $R_1$ is said aryloxy radical.

26. The process of claim 18 wherein $R_1$ is said aryloxy radical and all X's are H.

27. The process of claim 26 wherein n is 3, 4, or 5, and n' is 6.

28. The process of claim 18 wherein $R_1$ is said isopropoxy radical.

29. The process of claim 18 wherein $R_1$ is said isopropoxy radical and all Z's are H.

30. The process of claim 29 wherein n is 3, 4 or 5, and n' is 6.

31. The process of claim 27 wherein said $b \geq 14$-n-n'.

32. The process of claim 30 wherein said $b \geq 14$-n-n'.

33. The process of claim 21 wherein n is 3, 4, or 5, n' is 6 $R_1$ is said aryloxy radical and all X's are H and $b \geq 14$-n-n'.

34. The process of claim 21 wherein n is 3, 4, or 5, n' is 6, $R_1$ is said isopropoxy radical and all Z's are H and $b \geq 14$-n-n'.

35. Compounds of the formula,

wherein $R_1$ is an isopropoxy radical having the formula $$-O-CH-CZ_3$$
$$\phantom{-O-CH-}CZ_3$$

or an aryloxy radical having the formula

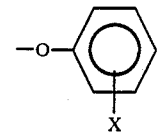

wherein each Z is independently selected for each isopropoxy radical from F and H, wherein each X is independently selected for each aryloxy radical from Cl, Br, F and H, and wherein n is a whole integer which is $\geq 1$ and $\leq 5$ when said compound has an m- or p- hydroxymethylphenoxy substituent and which is $\geq 3$ and $\leq 5$ when said compound has an o-hydroxymethylphenoxy substituent.

* * * * *